United States Patent
Igarashi

(10) Patent No.: US 11,412,113 B2
(45) Date of Patent: Aug. 9, 2022

(54) IMAGE PICKUP APPARATUS, ENDOSCOPE, AND MANUFACTURING METHOD OF IMAGE PICKUP APPARATUS

(71) Applicant: OLYMPUS CORPORATION, Tokyo (JP)

(72) Inventor: Takatoshi Igarashi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/079,628

(22) Filed: Oct. 26, 2020

(65) Prior Publication Data

US 2021/0099620 A1  Apr. 1, 2021

Related U.S. Application Data

(63) Continuation of application No. PCT/JP2018/017096, filed on Apr. 26, 2018.

(51) Int. Cl.
*H04N 5/225* (2006.01)
*H01L 27/146* (2006.01)
(Continued)

(52) U.S. Cl.
CPC ..... *H04N 5/2253* (2013.01); *H01L 27/14618* (2013.01); *H01L 27/14683* (2013.01);
(Continued)

(58) Field of Classification Search
CPC .............. H04N 5/2253; H04N 5/2254; H04N 2005/2255; H01L 27/14618;
(Continued)

(56) References Cited

U.S. PATENT DOCUMENTS

2012/0229908 A1  9/2012 Kintz et al.
2017/0027421 A1* 2/2017 Imai .................... A61B 1/0011
(Continued)

FOREIGN PATENT DOCUMENTS

JP    2011085625 A1   4/2011
JP    2013-037244 A   2/2013
(Continued)

OTHER PUBLICATIONS

International Search Report dated Aug. 7, 2018 issued in PCT/JP2018/017096.

*Primary Examiner* — Nasim N Nirjhar
(74) *Attorney, Agent, or Firm* — Scully, Scott, Murphy & Presser, P.C.

(57) ABSTRACT

An image pickup apparatus includes: a first member, in which a plurality of optical members are laminated; a second member including an image pickup device; and a third member including a spacer and a frame, a first through-hole that penetrates through the spacer and a second through-hole that has a larger sectional area in a direction that perpendicularly intersects an optical axis than a sectional area of the first through-hole and that penetrates through the frame are provided in the third member, the third member is glued to the first member, the second member is disposed in the second through-hole, and a front surface of the second member abuts on a second main surface of the spacer, and the frame is a frame body that shields light that is incident on the second through-hole from an image pickup side surface that is a side surface of the second member.

12 Claims, 9 Drawing Sheets

(51) Int. Cl.
*A61B 1/00* (2006.01)
*A61B 1/05* (2006.01)

(52) U.S. Cl.
CPC .......... *H04N 5/2254* (2013.01); *A61B 1/0011* (2013.01); *A61B 1/051* (2013.01); *H04N 2005/2255* (2013.01)

(58) Field of Classification Search
CPC . H01L 27/14683; A61B 1/0011; A61B 1/051; G02B 13/0085; G02B 23/243; G02B 7/02; G02B 23/24; G03B 17/02
See application file for complete search history.

(56) References Cited

U.S. PATENT DOCUMENTS

| | | |
|---|---|---|
| 2017/0374252 A1 | 12/2017 | Chen et al. |
| 2019/0373147 A1* | 12/2019 | Yamamoto ........... H04N 5/2254 |

FOREIGN PATENT DOCUMENTS

| | | |
|---|---|---|
| JP | 5474890 B2 | 4/2016 |
| WO | 2010/033211 A1 | 3/2010 |
| WO | 2010/101009 A1 | 9/2010 |
| WO | 2010/140395 A1 | 12/2010 |
| WO | 2017/203593 A1 | 11/2017 |

* cited by examiner

IMAGE PICKUP APPARATUS, ENDOSCOPE, AND MANUFACTURING METHOD OF IMAGE PICKUP APPARATUS

CROSS REFERENCE TO RELATED APPLICATION

This application is a continuation application of PCT/JP2018/017096 filed on Apr. 26, 2018, the entire contents of which are incorporated herein by this reference.

BACKGROUND OF THE INVENTION

1. Field of the Invention

The present invention relates to an image pickup apparatus provided with a laminated optical portion, an image pickup unit, and a holding portion, an endoscope including an image pickup apparatus provided with a laminated optical portion, an image pickup unit, and a holding portion, and a manufacturing method of an image pickup apparatus provided with a laminated optical portion, an image pickup unit, and a holding portion.

2. Description of the Related Art

Japanese Patent Application Laid-Open Publication No. 2013-37244 discloses an image pickup apparatus that accommodates, in a light shielding holder, a lens unit obtained by bonding and then cutting a lens wafer and a light shielding plate wafer and an image pickup device unit.

Diameters of endoscopes have been reduced to achieve minimal invasiveness. On the other hand, in order to insert microscopes into lumens with ultrasmall diameters, such as blood vessels or bronchioles, endoscopes with ultrasmall diameters are needed. However, it is not easy to obtain endoscopes with ultrasmall diameters that have insertion portions with diameters of less than 3 mm, for example, through extension of diameter reducing techniques for achieving minimal invasiveness.

International Publication No. 2017/203593 discloses an image pickup apparatus configured of a wafer level laminated body. The image pickup apparatus is manufactured by bonding a plurality of optical device wafers and an image pickup device wafer, then disposing a light shielding layer, and cutting the bonded optical device wafers and the image pickup device wafer on which the light shielding layer is disposed.

According to the aforementioned method, if defective image pickup devices are included in image pickup device wafers, manufactured image pickup apparatuses include defective products. Therefore, it is preferable to cut image pickup device wafers on which inspection has been conducted and to produce image pickup apparatuses using only non-defective products.

For image pickup apparatuses for endoscopes, it is preferable to manufacture a plurality of image pickup apparatuses provided with image pickup devices with different specifications at the same time since many models of endoscopes are to be manufactured in small quantities.

SUMMARY OF THE INVENTION

An image pickup apparatus according to an embodiment includes: a first member including an incident surface and an emission surface on an opposite side of the incident surface, in which a plurality of optical members are laminated; a second member including a front surface and a back surface on an opposite side of the front surface and including an image pickup device to which a cover glass is glued, and a third member including a spacer that includes a first main surface and a second main surface on an opposite side of the first main surface and a frame that includes a third main surface and a fourth main surface on an opposite side of the third main surface such that the third main surface faces the second main surface. A first through-hole that penetrates through the spacer and a second through-hole that has a larger sectional area in a direction that perpendicularly intersects an optical axis than a sectional area of the first through-hole and that penetrates through the frame are provided in the third member, the first main surface of the third member is glued to the emission surface of the first member, the second member is disposed such that at least a part of the second member is inserted into the second through-hole, and the front surface abuts on the second main surface of the spacer, and the frame is a frame body that shields light that is incident on the second through-hole from an image pickup side surface that is a side surface of the second member.

An endoscope according to an embodiment includes: an image pickup apparatus, in which the image pickup apparatus includes a first member including an incident surface and an emission surface on an opposite side of the incident surface, in which a plurality of optical members are laminated, a second member including a front surface and a back surface on an opposite side of the front surface and including an image pickup device to which a cover glass is glued, and a third member including a spacer that includes a first main surface and a second main surface on an opposite side of the first main surface and a frame that includes a third main surface and a fourth main surface on an opposite side of the third main surface such that the third main surface faces the second main surface. A first through-hole that penetrates through the spacer and a second through-hole that has a larger sectional area in a direction that perpendicularly intersects an optical axis than a sectional area of the first through-hole and that penetrates through the frame are provided in the third member, the first main surface of the third member is glued to the emission surface of the first member, the second member is disposed such that at least a part of the second member is inserted into the second through-hole, and the front surface abuts on the second main surface of the spacer, and the frame is a frame body that shields light that is incident on the second through-hole from an image pickup side surface that is a side surface of the second member.

A manufacturing method of an image pickup apparatus according to an embodiment includes: producing a laminated optical wafer, in which a plurality of first members are disposed in an array shape, each of the plurality of first members includes an incident surface and an emission surface on an opposite side of the incident surface, and a plurality of optical members are laminated; producing a holding wafer, in which a plurality of third members are disposed in an array shape, each of the plurality of third members includes a spacer including a first main surface and a second main surface on an opposite side of the first main surface and a frame including a third main surface and a fourth main surface on an opposite side of the third main surface such that the third main surface faces the second main surface, and a first through-hole that penetrates through the spacer and a second through-hole that has a larger sectional area in a direction that perpendicularly intersects an optical axis than a sectional area of the first through-hole and that penetrates through the frame are provided; producing a holding wafer with optical portions, in which the first main surface of each of the plurality of third members is glued to the emission surface of each of the plurality of first members, by gluing the laminated optical wafer and the holding wafer to each other; disposing at least some of second members, each of which includes a front surface and a back surface on an opposite side of the front surface and includes an image pickup device to which a cover glass is glued, at each of the plurality of third members of the holding wafer with the optical portions in a state in which at least the some of the second members are inserted into the second through-hole and the front surface abuts on the second main surface of the spacer; and cutting the holding wafer with the optical portions on which the plurality of second members are disposed.

DETAILED DESCRIPTION OF THE PREFERRED EMBODIMENTS

<Configuration of Endoscope>

Figure 1:
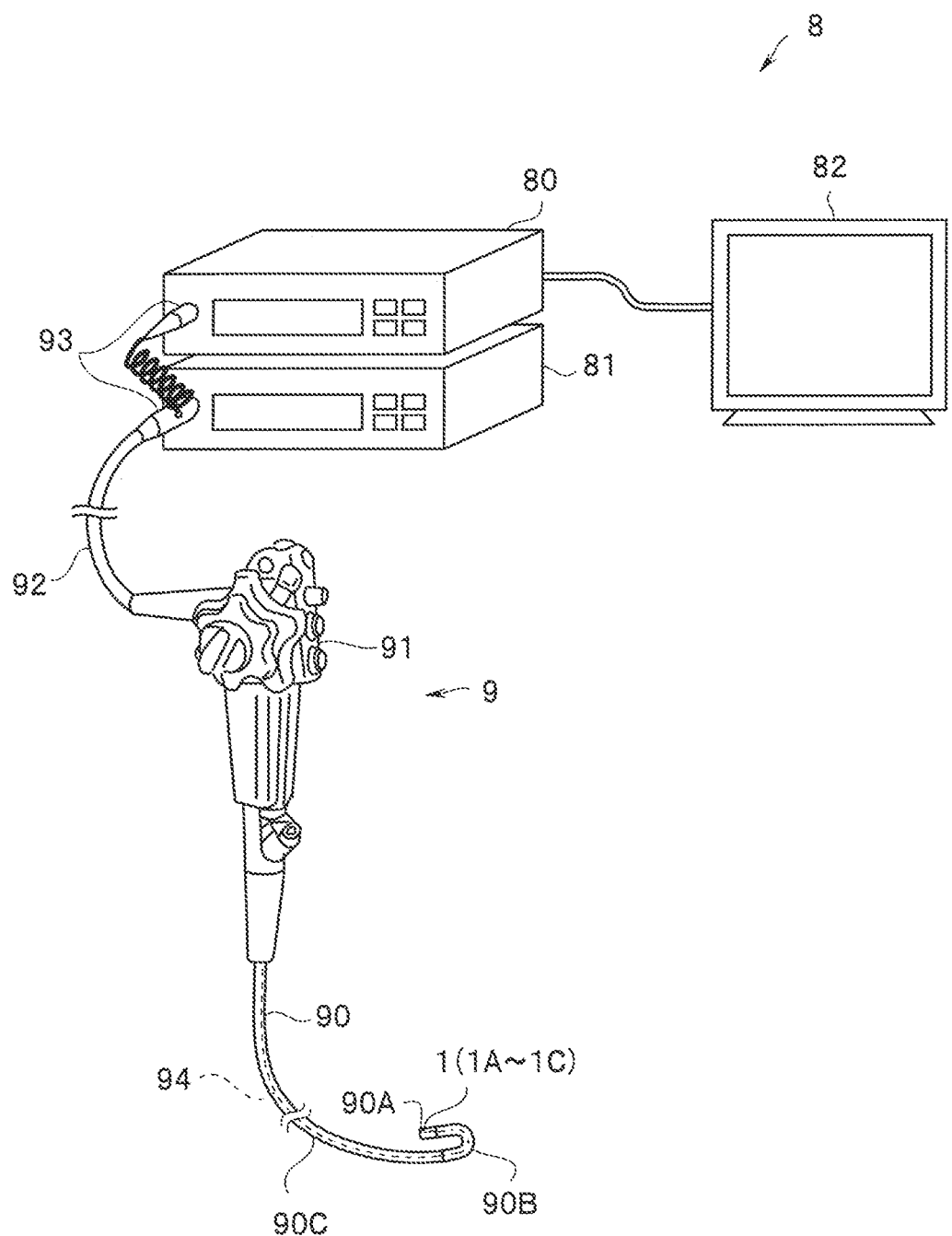
FIG. 1 is a perspective view of an endoscope system including an endoscope according to an embodiment.

As illustrated in FIG. 1, an endoscope system 8 including an endoscope 9 according to an embodiment is provided with the endoscope 9, a processor 80, a light source device 81, and a monitor 82. The endoscope 9 includes an insertion portion 90, an operation portion 91, and a universal cord 92. The endoscope 9 is adapted such that an insertion portion 90 is inserted into a body cavity of a subject to photograph an image inside the body of the subject and output an image signal.

The insertion portion 90 is configured of a distal end portion 90A at which an image pickup apparatus 1 is disposed, a bending portion 90B that is continuously provided at a proximal end portion of the distal end portion 90A to be bendable, and a flexible portion 90C that is continuously provided at a proximal end portion of the bending portion 90B. The bending portion 90B is bent in response to an operation of the operation portion 91. Note that although the endoscope 9 is a flexible endoscope for medical use, the endoscope 9 may be a rigid endoscope, may be an endoscope for industrial use, or may be an endoscope of a capsule type.

The operation portion 91 in which various buttons for operating the endoscope 9 are provided is disposed at a proximal end portion of the insertion portion 90 of the endoscope 9.

The light source device 81 includes, for example, a white LED. Illumination light that the light source device 81 emits is guided to the distal end portion 90A by passing through a light guide (not illustrated) that allows insertion of the universal cord 92 and the insertion portion 90 to illuminate the subject.

The endoscope 9 transmits an image pickup signal that the image pickup apparatus 1 disposed at the distal end portion 90A of the insertion portion 90 outputs via a signal cable 94 that allows insertion of the insertion portion 90.

Since the image pickup apparatus 1 for an endoscope has an ultrasmall size, and the distal end portion 90A of the insertion portion 90 thus has a diameter of less than 3 mm, for example, the endoscope 9 is minimally invasive.

First Embodiment

Figure 2:
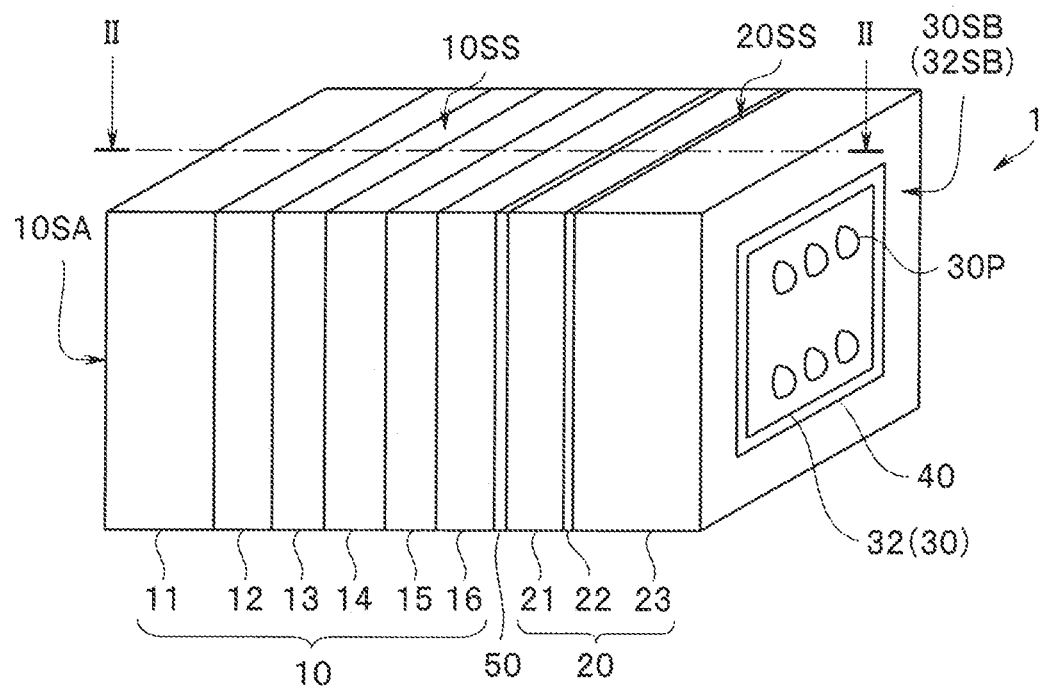
FIG. 2 is a perspective view of an image pickup apparatus according to a first embodiment.
Figure 3:
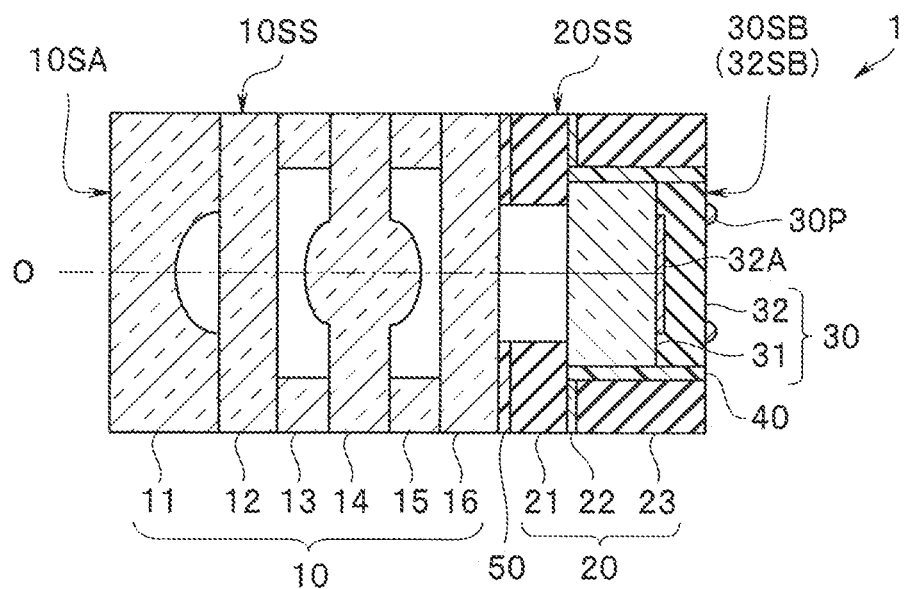
FIG. 3 is a sectional view of the image pickup apparatus according to the first embodiment along the line II-II in FIG. 2.
Figure 4:
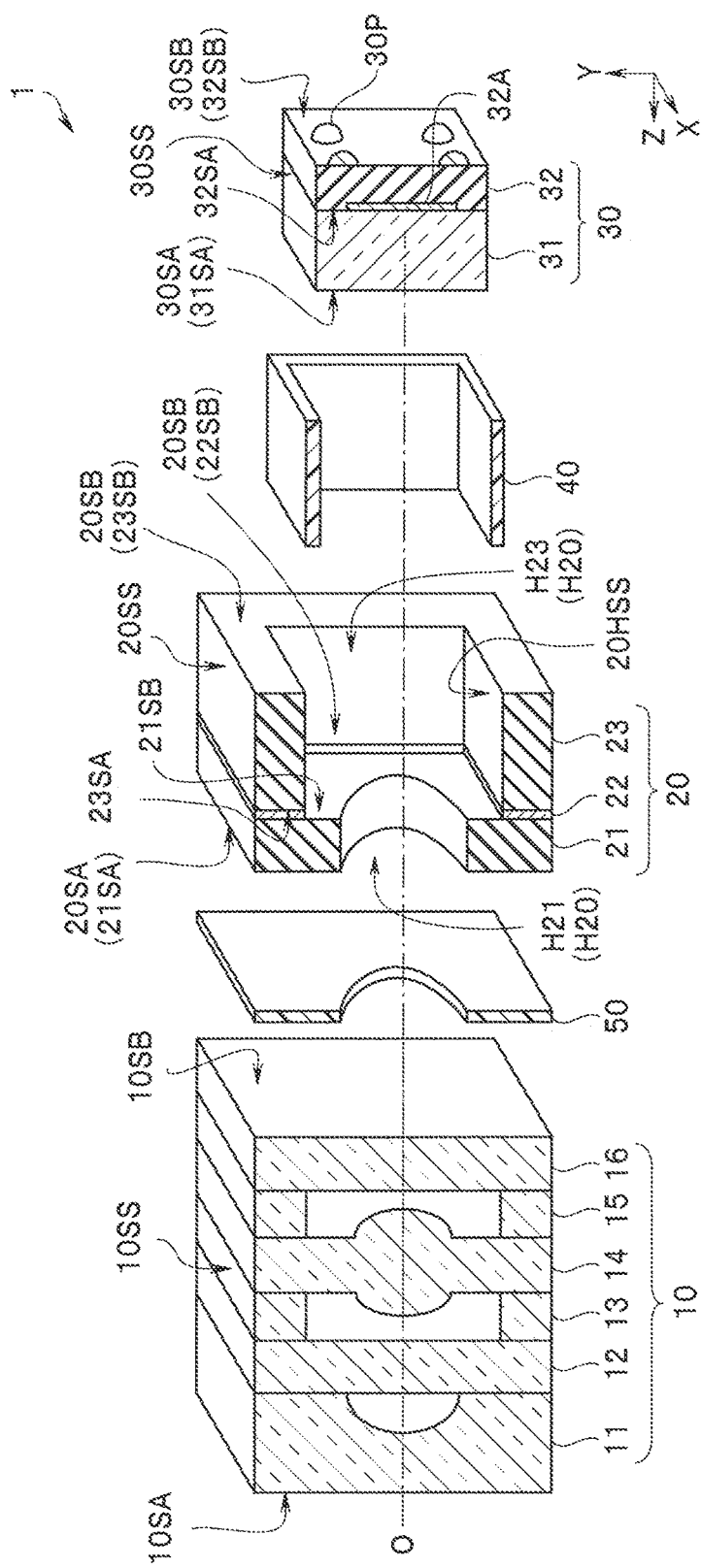
FIG. 4 is a sectional perspective exploded view of the image pickup apparatus according to the first embodiment.

As illustrated in FIGS. 2 to 4, the image pickup apparatus 1 according to the embodiment is provided with a laminated optical portion (first member) 10, an image pickup unit (second member) 30, and a holding portion (third member: holder) 20.

It should be noted that in the following description, the drawings based on each embodiment are schematically illustrated and relationships between thicknesses and widths of the respective portions, ratios of the thicknesses of the respective portions, relative angles, and the like are different from actual relationships, ratios, relative angles, and the like, and there may be a case in which portions with mutually different dimensional relationships or ratios are included across drawings. Illustration and application of reference signs may be omitted for a part of components. A direction in which the subject is disposed in an optical axis direction will be referred to as "front", and a direction in which the image pickup unit 30 is disposed will be referred to as "back".

The laminated optical portion 10 in which a plurality of optical members 11 to 16 are laminated is an optical part that includes an incident surface (front surface) 10SA on which light is incident and an emission surface (back surface) 10SB on the opposite side of the incident surface 10SA.

The optical members 11 and 14 are lens members. The optical member 16 is a parallel flat plate filter made of an infrared cutting material that removes infrared rays. The optical members 13 and 15 are spacers in which portions that serve as optical paths are through-holes.

As will be described later, the laminated optical portion 10 that is a wafer level laminated body has a rectangular parallelepiped shape that has, as a cut surface, an optical side surface 10SS that is a side surface.

The image pickup unit 30 that includes a cover glass 31 and an image pickup device 32 includes a front surface 30SA (cover glass front surface 31SA) and a back surface 30SB on the opposite side of the front surface 30SA, and a plurality of external electrodes 30P are disposed on the back surface 30SB (image pickup device back surface 32SB).

The image pickup device 32 includes a light receiving portion 32A that is configured of a CCD or CMOS image pickup unit, and the light receiving portion 32A is connected to a penetrating wiring (not illustrated). The image pickup device 32 may be either a front surface irradiation-type image sensor or a back surface irradiation-type image sensor. The light receiving portion 32A is connected to the external electrodes 30P on the back surface 30SB via the penetrating wiring. Although not illustrated, the external electrodes 30P are electrically connected to the signal cable 94.

As will be described later, the image pickup unit 30 that is a wafer level laminated body has a rectangular parallelepiped shape that has, as a cut surface, an image pickup side surface 30SS that is a side surface.

The holding portion 20 is made of Silicon on Insulator (SOI) including a spacer 21, a frame 23, and a silicon oxide layer 22 that is an intermediate layer. In other words, the spacer 21 made of silicon has a first main surface 21SA and a second main surface 21SB on an opposite side of the first main surface 21SA. The frame 23 made of silicon has a third main surface 23SA and a fourth main surface 23SB on an opposite side of the third main surface 23SA. The silicon oxide layer 22 that is an insulating layer bonds the second main surface 21SB and the third main surface 23SA In other words, the third main surface 23SA and the second main surface 21SB face each other.

As will be described later, the holding portion 20 produced from an SOT wafer has a rectangular parallelepiped shape that has, as a cut surface, a holding side surface 20SS that is a side surface.

The holding portion 20 is a frame body in which a first through-hole H21 that penetrates through the spacer 21, a second through-hole H23 that penetrates through the frame 23, and a third through-hole H22 that penetrates through the silicon oxide layer 22. A through-hole H20 that penetrates through the holding portion 20 is configured by the first through-hole H21, the second through-hole H23, and the third through-hole 122. In other words, the first through-hole H21, the second through-hole H23, and the third through-hole H22 communicate with each other, and these form an optical path between the laminated optical portion 10 and the image pickup unit 30. Also, the diameter of the first through-hole H21 is substantially the same as the outer dimension of the light receiving portion 32A. On the other hand, the inner dimension of the second through-hole H23 is slightly larger than the outer dimension of the image pickup unit 30.

The second through-hole H23 and the third through-hole H22 have larger sectional areas in a direction that perpendicularly intersects an optical axis than the sectional area of the first through-hole H21. The first through-hole H21 has a circular section in the direction that perpendicularly intersects the optical axis, and the second through-hole H23 and the third through-hole H22 have rectangular sections.

A first main surface 20SA (21SA) of the holding portion 20 is glued to the emission surface 10SB of the laminated optical portion 10 with an adhesive layer 50.

The image pickup unit 30 is disposed in the second through-hole H23 and the third through-hole H2, and the front surface 30SA of the image pickup unit 30 abuts on the second main surface 21SB of the spacer 21. An adhesive 40 is disposed between the image pickup side surface 30SS and a wall surface 20HSS of the second through-hole H23 while no adhesive 40 is disposed between the front surface 30SA and the second main surface 21SB. In other words, the front surface 30SA and the second main surface 21SB are in direct surface contact with each other with no other member interposed between the front surface 30SA and the second main surface 21SB.

The image pickup apparatus 1 has a square sectional shape that perpendicularly intersects an optical axis O, for example, and the dimension (outer dimension) is as ultrasmall as 1 mm square or less. The dimension (outer dimension) of the image pickup unit 30 in the direction that perpendicularly intersects the optical axis is, for example, 0.5 mm square or less. Therefore, it is not easy to dispose the image pickup unit 30 directly on the emission surface 10SB of the laminated optical portion 10. On the other hand, it is easy to insert the image pickup unit 30 into the second through-hole H23 of the holding portion 20 even if the size of the image pickup unit 30 is small. Further, positioning of the image pickup unit 30 in an in-plane direction (XY direction: see FIG. 4) that perpendicularly intersects the optical axis is automatically performed by inserting the image pickup unit 30 into the second through-hole H23.

The position of the light receiving portion 32A (light receiving surface 32SA) of the image pickup unit 30 in the direction of the optical axis O (Z direction: see FIG. 4) is preferably positioned with precision of an error of 1 μm or less, for example, relative to the focal position of the laminated optical portion 10 in order to obtain a satisfactory image.

In the image pickup apparatus 1, the distance from the emission surface 10SB of the laminated optical portion 10 to the light receiving portion 32A is defined by the thickness of the adhesive layer 50 and the thickness of the spacer 21. It is possible to easily realize the production of the adhesive layer 50 and the spacer 21 with thicknesses with precision of an error of 1 μm or less using a known spin coating technique for the adhesive layer 50 or a known polishing technique for the spacer 21. Therefore, the position of the light receiving portion 32A (light receiving surface 32SA) in the direction of the optical axis is positioned with precision of an error of 1 μm or less, for example, relative to the focal position of the laminated optical portion 10 by the front surface 30SA of the image pickup unit 30 abutting on the second main surface 21SB of the spacer 21 in the image pickup apparatus 1. Therefore, the image pickup apparatus 1 has high performance.

The frame 23 made of silicon has a light shielding function of shielding unnecessary light that is incident on an optical path (second through-hole H23) from the image pickup side surface 30SS of the image pickup unit 30. The image pickup apparatus 1 is not affected by external light and stray light and thus has high performance.

Further, there is no concern that peeling of the adhesive layer 50 occurs due to a stress in the direction that perpendicularly intersects the optical axis in the image pickup unit 30 disposed in the second through-hole H23. In other words, since the frame 23 also has a reinforcing function of improving mechanical strength of the image pickup unit 30, image pickup apparatus 1 has high reliability.

Note that the back surface 30SB of the image pickup unit 30 may project from the second through-hole 23 as long as a part of the image pickup device 32 is accommodated in the second through-hole H23. In other words, it is only necessary for the image pickup unit 30 to be disposed such that at least a part of the image pickup unit 30 is inserted into the second through-hole H23. The thickness (the dimension in the direction of the optical axis: the depth of the second through-hole) of the frame 23 may be smaller than the thickness of the image pickup unit 30. It is a matter of course that the entire image pickup unit 30 may be fully accommodated in the second through-hole H23.

The image pickup apparatus 1 has a ultrasmall size and high performance and can easily be manufactured, and the endoscope 9 including the image pickup apparatus 1 is minimally invasive, has high performance, and can easily be manufactured. As a material of the spacer and the frame, glass, resin, metal, or the like may be used instead of silicon.

<Manufacturing Method of Image Pickup Apparatus>

Figure 5:
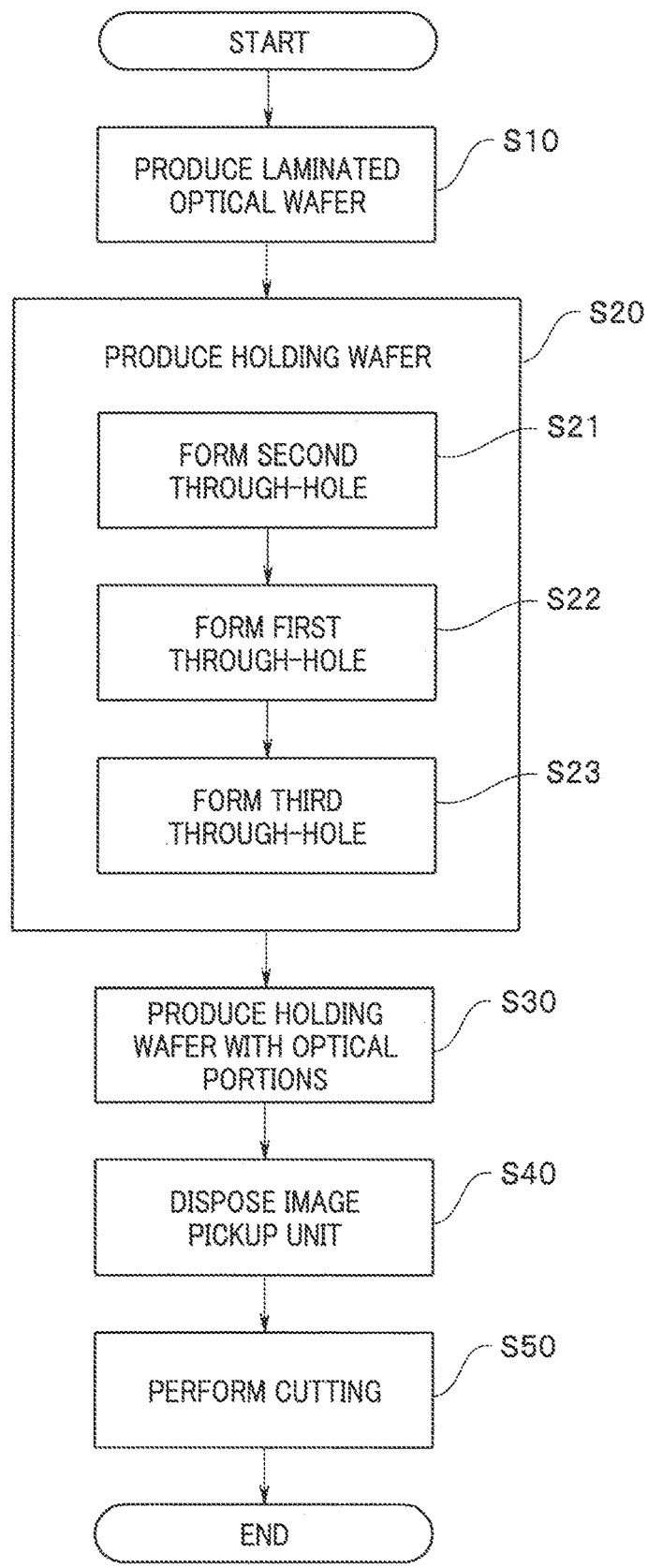
FIG. 5 is a flowchart of a manufacturing method of the image pickup apparatus according to the first embodiment.

A manufacturing method of the image pickup apparatus will be described in accordance with the flowchart in FIG. 5.

<Step S10> Laminated Optical Wafer Production Process (First Process)

Figure 12:
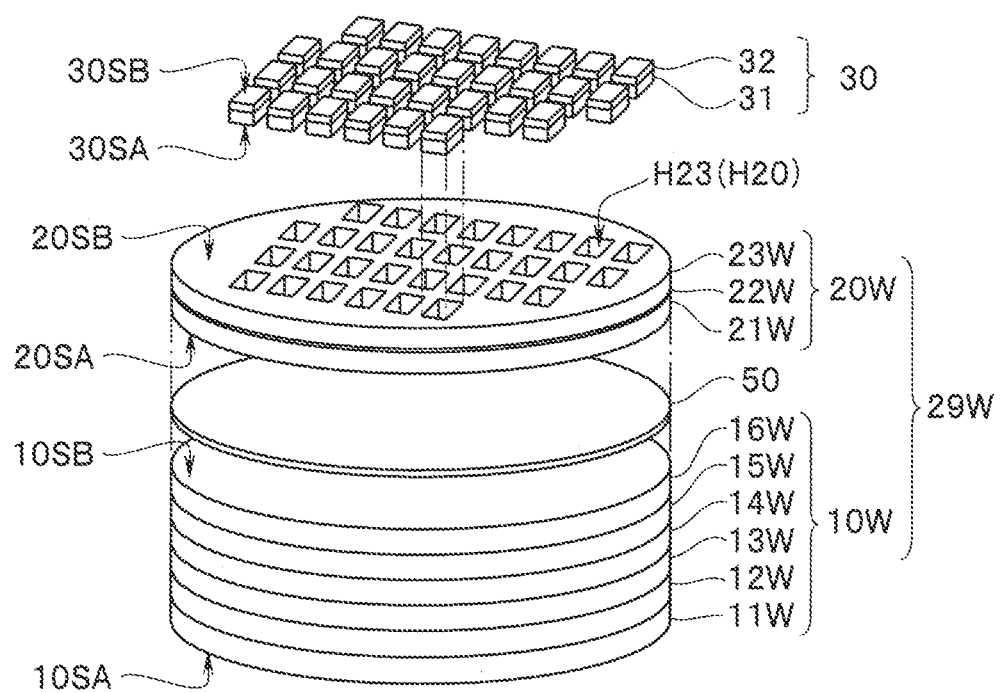
FIG. 12 is a perspective exploded view for explaining the manufacturing method of the image pickup apparatus according to the first embodiment.

Optical wafers 11W to 16W in which the plurality of optical members 11 to 16 are formed, respectively, are produced (see FIG. 12). For example, the optical wafers 11W and 14W are lens wafers formed through resin molding. The optical wafers 11W and 14W may be hybrid lens wafers in each of which a plurality of resin lenses are disposed on a glass substrate. The optical wafer 16W is a parallel flat plate filter wafer made of an infrared cutting material that removes infrared rays. As the filter wafer, a transparent wafer in which a bandpass filter that transmits only light with a predetermined wavelength and cuts light with unnecessary wavelengths is disposed on the surface may be used. The optical wafers 13W and 15W are spacer wafers in which portions that serve as optical paths are through-holes.

The optical wafers 11W to 16W are glued to each other with a transparent adhesive or are bonded directly to each other, thereby producing the laminated optical wafer 10W with a thickness of 3000 μm, for example. Note that types, materials, shapes (circular shapes, rectangular shapes), thicknesses, the number of laminations, and the order of laminations of the plurality of optical wafers can appropriately be changed.

<Step S20> Holding Wafer Production Process (Second Process)

A holding wafer 20W in which a plurality of the holding portions 20 are disposed in an array shape (two-dimensional matrix shape) is produced.

The second process includes a process (Step S21) of forming the second through-hole H23, a process (Step S22) of forming the first through-hole H21, and a process (Step S23) of forming the third through-hole 122.

In the manufacturing method, the holding wafer 20W is produced through etching of an SOI wafer 20WA including a silicon layer (active layer) 21W, a silicon oxide layer 22W, and a silicon substrate 23W.

<Step S21> Second Through-Hole Formation Process

Figure 6:
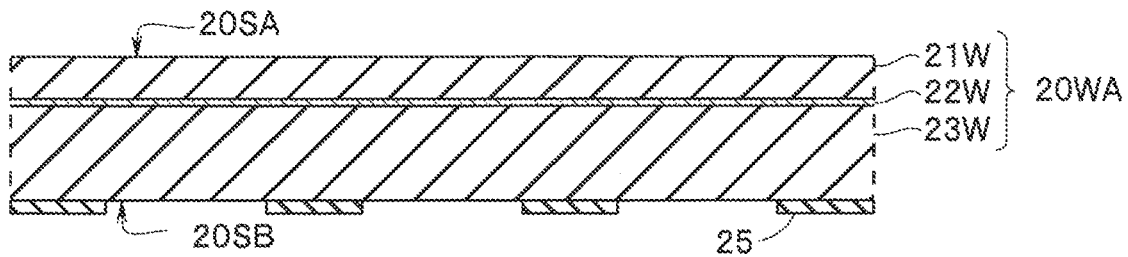
FIG. 6 is a sectional view for explaining the manufacturing method of the image pickup apparatus according to the first embodiment.

As illustrated in FIG. 6, an etching mask 25 made of silicon oxide or photoresist is disposed on a second main surface 20SB of the SOI wafer WA.

Figure 7:
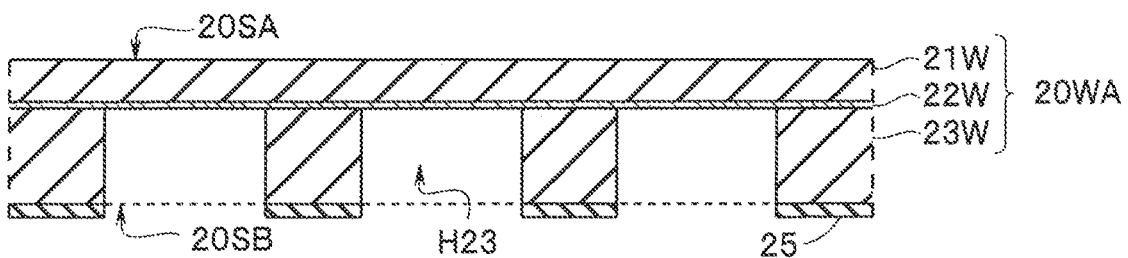
FIG. 7 is a sectional view for explaining the manufacturing method of the image pickup apparatus according to the first embodiment.

The second through-hole H23 with a rectangular section that penetrates through the silicon substrate 23W is formed as illustrated in FIG. 7 by successively repeating a protective film formation process in which protective film formation gas is introduced and an etching process in which etching gas is introduced. For example, the protective film formation gas is $C_4F_8$, and etching gas is $SF_6$. Since the silicon oxide layer 22W serves as an etching stop layer, the formed second through-hole H23 uses the silicon oxide layer 22W as a bottom surface.

<Step S22> First Through-Hole Formation Process

Figure 8:
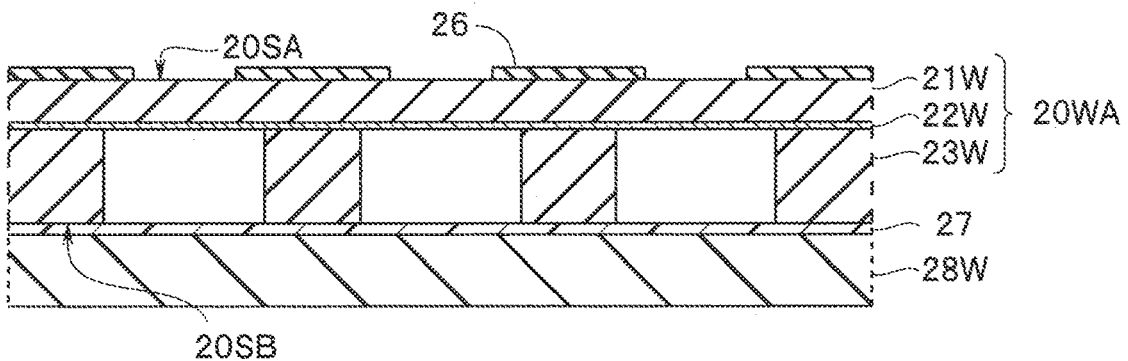
FIG. 8 is a sectional view for explaining the manufacturing method of the image pickup apparatus according to the first embodiment.

As illustrated in FIG. 8, a support plate 28W including an adhesive layer 27 is glued to the second main surface 20SB of the SOI wafer 20WA. Then, an etching mask 26 made of silicon oxide or photoresist is disposed on the first main surface 20SA of the SOI wafer 20WA.

Figure 9:
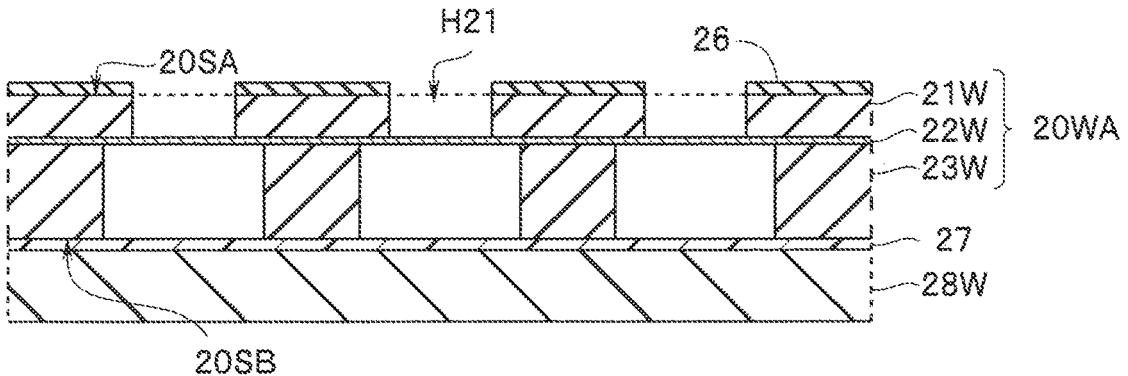
FIG. 9 is a sectional view for explaining the manufacturing method of the image pickup apparatus according to the first embodiment.

As illustrated in FIG. 9, the first through-hole H21 with a circular section is formed in the silicon layer 21W. The formed first through-hole H21 uses the silicon oxide layer 22W as a bottom surface.

Figure 10:
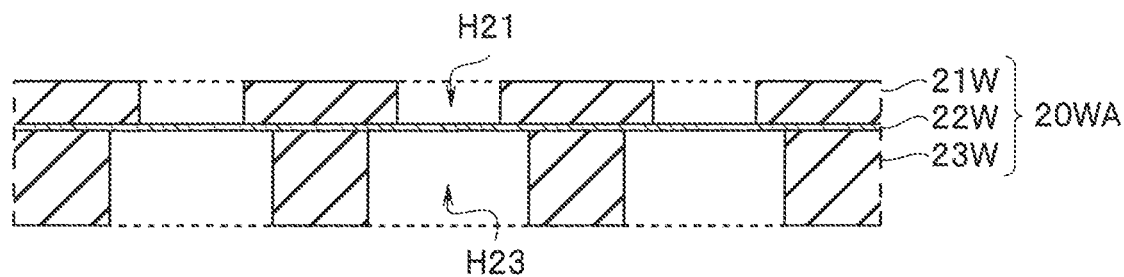
FIG. 10 is a sectional view for explaining the manufacturing method of the image pickup apparatus according to the first embodiment.

As illustrated in FIG. 10, the support plate 28W is detached from the SOI wafer 20WA. The adhesive layer 27 loses an adhesive force through irradiation with ultraviolet rays, heating, or immersion in a solvent.

<Step S23> Third Through-Hole Formation Process

Figure 11:
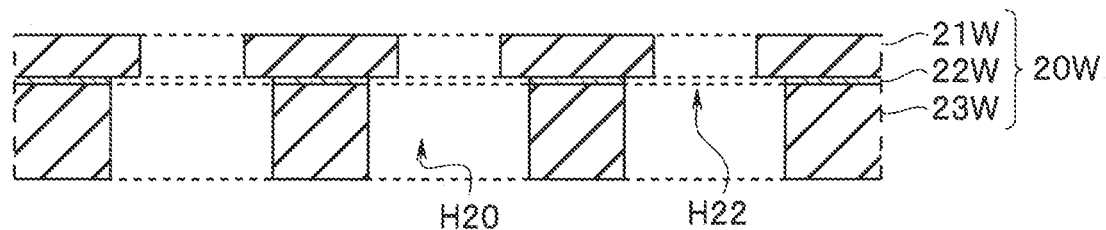
FIG. 11 is a sectional view for explaining the manufacturing method of the image pickup apparatus according to the first embodiment.

As illustrated in FIG. 11, the silicon oxide layer 22W at the bottom surface of the first through-hole H21 (the bottom surface of the second through-hole H23) is removed, and the third through-hole H22 is formed, thereby forming the through-hole H20 in the holding portion 20.

For example, the holding wafer 20W is produced by removing the silicon oxide layer 22W at the bottom surface using a hydrofluoric acid solution that has a higher etching rate for silicon oxide than an etching rate for silicon. Note that the third through-hole H22 has the same shape and the same size as the shape and the size of the second through-hole H23.

The second through-hole formation process (S21) may be performed after the first through-hole formation process (S22). In a case in which the etching masks 25 and 26 are silicon oxide, the etching masks 25 and 26 may be removed in the third through-hole formation process (S23). The laminated optical wafer production process (first process) may be performed after the holding wafer production process (second process).

<Step S30> Production of Holding Wafer with Optical Portions (Third Process)

As illustrated in FIG. 12, the holding wafer 29W with the optical portion is produced by gluing the emission surface 10SB of the laminated optical wafer OW and the first main surface 20SA of the holding wafer 20W to each other with the adhesive layer 50. Note that although all the respective wafers illustrated in FIG. 12 have circular shapes, at least some of the wafers may have rectangular shapes, for example.

Note that in a case in which the thickness of the adhesive layer 50 spin-coated on the emission surface 10SB is 1 μm, for example, a thickness error of the adhesive layer 50 is 0.1 μm or less.

A through hole is preferably formed in advance in the optical path region in the adhesive layer 50. For example, the adhesive layer 50 is pattern-applied by an ink jet method or a metal mask method, or the adhesive layer 50 is glued using a resin containing a photoresist as the adhesive layer 50, and the adhesive layer 50 in the optical path region is then removed.

<Step S40> Image Pickup Unit Disposition Process (Fourth Process)

Although not illustrated, the image pickup unit 30 is produced by cutting a glass wafer, an image pickup device wafer, and an image pickup wafer. For example, the image pickup device wafer in which a plurality of the light receiving portions 32A are disposed is produced using a known semiconductor manufacturing technique for a silicon wafer. A peripheral circuit that performs primary processing on signals outputted from the light receiving portions 32A or performs processing on drive control signals may be formed in the image pickup device wafer.

In order to protect the light receiving portions 32A of the image pickup device wafer, a glass wafer made of a flat plate glass with a thickness of 250 μm, for example, is glued to the image pickup device wafer, thereby producing the image pickup wafer. A penetrating wiring connected to the light receiving portions 32A and the external electrodes 30P on the back surface 30SB are formed in the image pickup wafer.

Then, the image pickup unit 30 is produced by cutting the image pickup wafer. Therefore, four side surfaces (image pickup side surfaces 30SS) of the image pickup unit 30 are cut surfaces.

As illustrated in FIG. 12, a plurality of image pickup units 30 are disposed in the respective through-holes H20 in the holding wafer 29W with the optical portion. The outer dimension of each image pickup unit 30 (the section size in the direction that perpendicularly intersects the optical axis) is smaller than the second through-hole H23 (third through-hole H22) in the frame 23 and is larger than the first through-hole H21 in the spacer 21. Therefore, the front surface 30SA of the image pickup unit 30 abuts on the second main surface 21SB of the spacer 21.

Although each image pickup unit 30 is as ultrasmall as 0.5 mm square or less, for example, it is easy to dispose the image pickup unit 30 at a predetermined position in the in-plane direction (XY direction) of the holding wafer 29W with the optical portion since the second through-hole H23 is provided. The ultraviolet curable adhesive 40, for example, is disposed between the image pickup side surface 30SS and the wall surface 20HSS of the second through-hole H23, and curing processing using irradiation with ultraviolet rays is performed. The adhesive 40 may be a thermosetting adhesive or may be an adhesive that is cured through irradiation with ultraviolet rays and heating, or two types, namely the ultraviolet curable adhesive and the thermosetting adhesive may be used in combination.

Note that the section of the first through-hole H21 may have a rectangular shape. However, the section of the first through-hole H21 preferably has a circular shape for easiness of widening the area of an abutting surface between the front surface 30SA of the image pickup unit 30 and the second main surface 21SB of the spacer 21. If the first through-hole H21 of the spacer 21 has a circular shape with a diameter of 0.50 mm, for example, it is possible to cause the front surface 30S of the image pickup unit 30 with a square shape with a side of 0.50 mm to abut on the second main surface 21SB of the spacer 21.

Note that positioning of the image pickup unit 30 in the in-plane direction that perpendicularly intersects the optical axis, that is, position matching between the optical axis and the center of each light receiving portion 32A can be defined merely by disposing the image pickup unit 30 in the second through-hole H23. If the image pickup side surface 30SS of the parallelepiped shape and the wall surface 20HSS of the second through-hole H23 with a rectangular section are separated from each other by 5 μm, for example, positioning with precision of 2.5 μm is automatically performed. Therefore, the section of the second through-hole H23 preferably has a rectangular shape.

In a case in which more precise position matching is needed, the position of the image pickup unit 30 inserted into the second through-hole H23 is finely adjusted, and then adhesion is performed.

The thickness of the silicon layer 21W that serves as the spacer 21 is set on the basis of the focal position of the laminated optical portion 10. In a case in which the focal position is located at 50 μm from the emission surface 10SB, and the thickness of the adhesive layer 50 is 1 μm, for example, the thickness of the silicon layer 21W is set to 49 μm.

It is possible to easily perform positioning for the position of the light receiving portion 32A (light receiving surface 32SA) in the direction of the optical axis (Z direction: see FIG. 4) relative to the focal position of the laminated optical portion 10 with precision of an error of 1 μm or less by causing the front surface 30SA of the image pickup unit 30 to abut on the second main surface 21SB of the spacer 21 in the image pickup apparatus 1.

In a case in which there is a concern that the focal position of the laminated optical portion 10 is not defined at a constant position in the manufacturing process of the laminated optical wafer 10W, it is preferable to further include a measurement process (Step S15) of measuring the focal position of the laminated optical portion 10 after the production of the laminated optical wafer 10W and a polishing process (Step S16) of working the silicon layer 21W that serves as the spacer 21 of the holding wafer 20W into a predetermined thickness on the basis of the measured focal position. The polishing process is preferably performed prior to the process (S20) of forming the through-hole H20 in the SOI wafer 20WA.

In a case in which the focal position of the laminated optical portion 10 is located at 45 μm from the emission surface 10SB, and the thickness of the adhesive layer 50 is 1 μm, for example, the silicon layer 21W with the thickness of 49 μm is polished to have a thickness of 44 μm.

Note that a plurality of image pickup units with different specifications may be disposed in one holding wafer 29W with the optical portion. In order to accommodate the image pickup units with different sizes, a plurality of second through-holes with different sizes may be formed in the holding wafer.

<Step S50> Cutting Process (Fifth Process)

Figure 13:
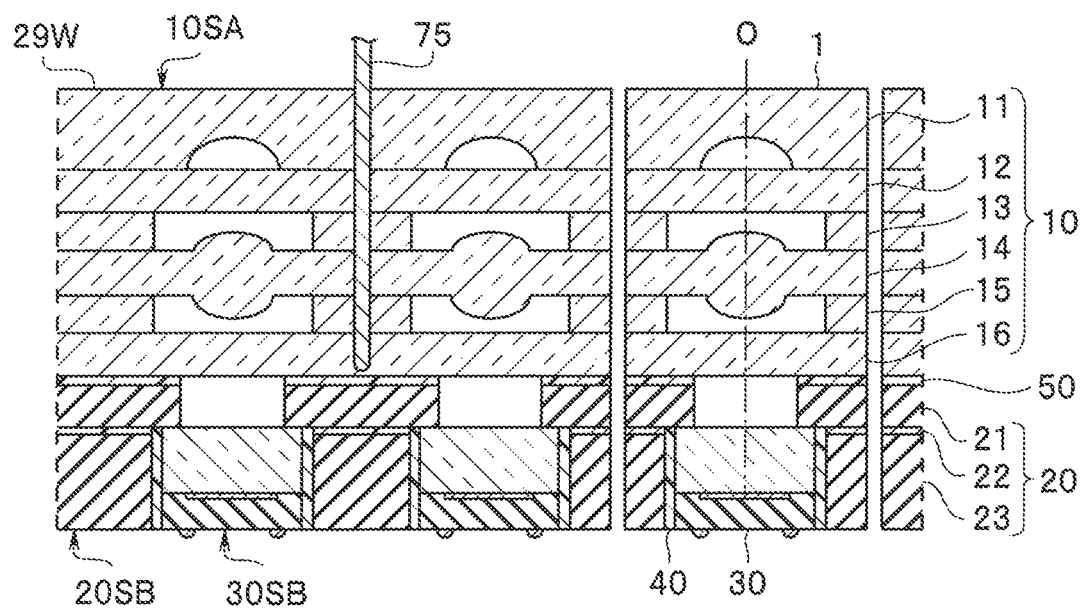
FIG. 13 is a sectional view for explaining the manufacturing method of the image pickup apparatus according to the first embodiment.

As illustrated in FIG. 13, a plurality of the image pickup apparatuses 1 are produced by cutting the holding wafer 29W with optical portions on which the plurality of image pickup units 30 are disposed using a dicing blade 75.

The laminated optical portion 10 and the holding portion 20 are cut in the same cutting process. Therefore, the optical side surface 10SS that is a side surface of the laminated optical portion 10 and the holding side surface 20SS that is a side surface of the holding portion 20 are in the same plane. Further, since the optical side surface 10SS and the holding side surface 20SS are cut surfaces, continuous cut marks are included in both the optical side surface 10SS and the holding side surface 20SS. The cut marks are minute linear irregularities generated on the cut surfaces in the dicing.

It is a matter of course that the silicon oxide layer 22 is also cut at the same time with the laminated optical portion 10 and the holding portion 20. Therefore, the side surface of the silicon oxide layer 22 is in the same plane as the optical side surface 10SS and the holding side surface 20SS and includes a continuous cut mark.

According to the manufacturing method of the image pickup apparatus 1, it is possible to easily manufacture the ultrasmall image pickup apparatus 1.

Modifications of First Embodiment

Various modifications can be made for the holding portion 20.

Figure 14:
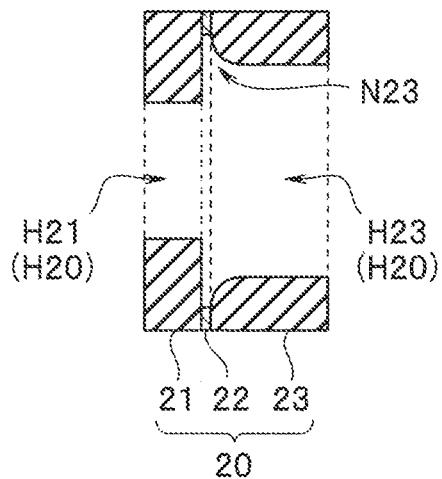
FIG. 14 is a sectional view of a holding portion of an image pickup apparatus according to a first modification of the first embodiment.

In the holding portion 20 according to the first modification illustrated in FIG. 14, a notch (recession) N23 is provided at an outer peripheral edge of an opening of the second through-hole H23 in the third main surface 23SA of the frame 23. The notch N23 that is a cut portion is an overetched region formed when the second through-hole H23 is formed.

The notch N23 can effectively prevent the adhesive 40 from entering the abutting surface between the front surface 30SA and the second main surface 21SB when the uncured adhesive 40 is poured between the image pickup side surface 30SS and the wall surface 20HSS of the second through-hole H23. In other words, since the excessive adhesive 40 is accommodated in the notch N23 and does not spread on the abutting surface.

Figure 15:
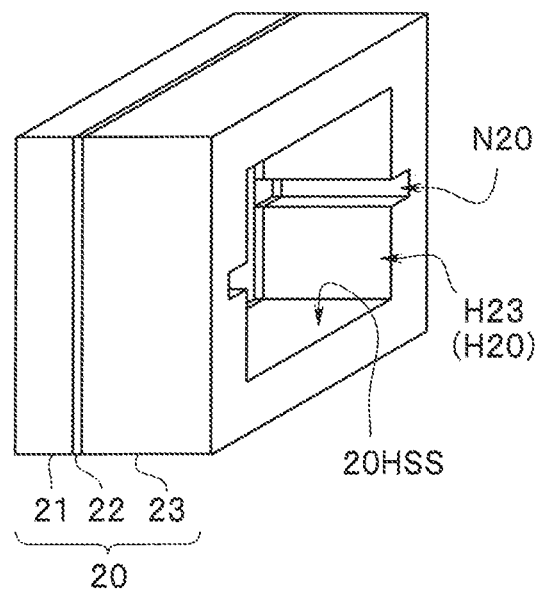
FIG. 15 is a sectional view of a holding portion of an image pickup apparatus according to a second modification of the first embodiment.

In the holding portion 20 according to the second modification illustrated in FIG. 15, a notch N20 that is parallel to the optical axis is provided in the wall surface 20HSS of the second through-hole H23 in the frame 23. The notch N20 is a groove in the wall surface 20HSS extending from the fourth main surface 23SB of the frame 23 to the second main surface 21SB of the spacer 21.

Since the second through-hole H23 and the image pickup unit 30 have substantially the same sizes, there may be a case in which it is not easy to dispose the adhesive 40 in the gap. However, it is easy to secure the image pickup unit 30 to the second through-hole H23 by pouring the adhesive 40 into the notch N20. Note that it is not necessary for the portion between the second through-hole H23 and the image pickup unit 30 to be filled with the adhesive 40 with no gap, and it is possible to secure the image pickup unit 30 to the second through-hole H23 as long as the adhesive 40 is disposed at least in a part of the notch N20.

A small amount of ultraviolet curable resin may be disposed in the notch N20 to temporarily secure the image pickup unit 30 to the second through-hole H23 after the image pickup unit 30 is inserted into the second through-hole H23 and positioning in the in-plane direction is performed. The adhesive 40 may be disposed after all the image pickup units 30 are temporarily secured to the holding wafer 29W with optical portions.

Note that although it is only necessary for the holding portion 20 to include at least one notch N20 in the wall surface 20HSS, a plurality of notches N20 may be provided.

The shape of the notch N20 is not limited to the shape in the illustrated example and may be a curved shape or the like.

Second Embodiment

Note that since image pickup apparatuses 1A to 1C according to the following embodiments are similar to the image pickup apparatus 1 and have similar advantages, the same reference signs will be applied to components with the same functions, and description will be omitted.

Figure 16:
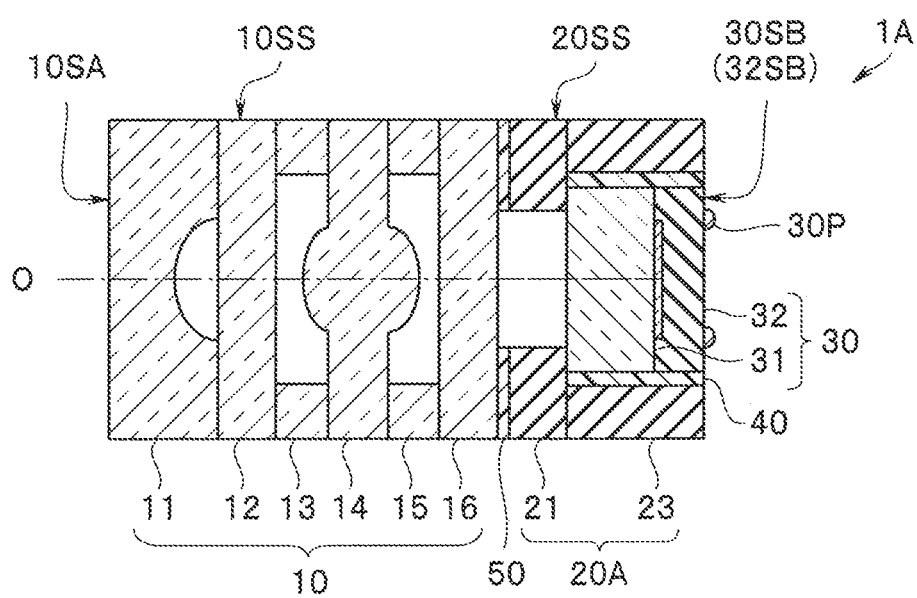
FIG. 16 is a sectional view of an image pickup apparatus according to a second embodiment.

The image pickup apparatus 1A illustrated in FIG. 16 includes no silicon oxide layer between a spacer 21 and a frame 23 of a holding portion 20A.

In the image pickup apparatus 1A, a holding wafer 20W is produced through bonding of two silicon wafers. For example, a first silicon wafer in which a first through-hole H21 is formed and a second silicon wafer in which a second through-hole H23 is formed are bonded directly to each other, thereby producing the holding wafer 20W. In other words, the silicon oxide layer is not an essential component of the holding wafer 20W (holding portion 20).

In other words, it is only necessary for the holding portion to include the spacer 21 and the frame 23.

Third Embodiment

Figure 17:
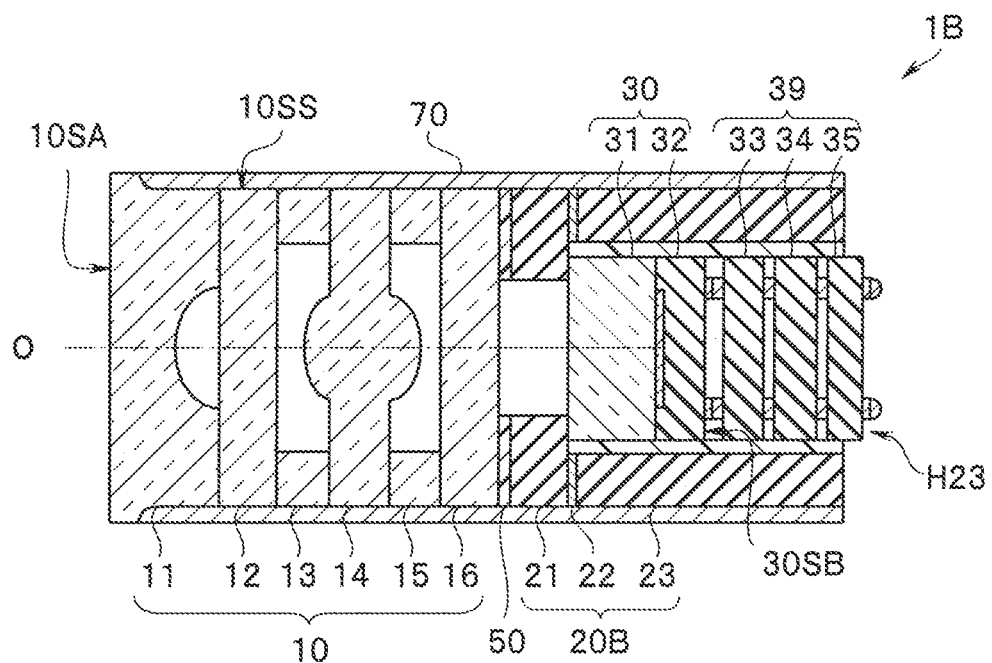
FIG. 17 is a sectional view of an image pickup apparatus according to a third embodiment.

The image pickup apparatus 1B illustrated in FIG. 17 further includes a laminated semiconductor 39 bonded to a back surface 30SB of an image pickup unit 30. The laminated semiconductor 39 in which a plurality of semiconductor devices 33 to 35 are laminated is disposed in a second through-hole H23.

The semiconductor devices 33 to 35 perform primary processing on image pickup signals outputted from an image pickup device 32 and perform processing on control signals for controlling the image pickup device 32. For example, the semiconductor devices 33 to 35 include an AD conversion circuit, a memory, a transmission output circuit, a filter circuit, a capacitor, a resistor, or an inductor. The number of semiconductor devices included in the laminated semiconductor 39 is, for example, equal to or greater than one and equal to or less than ten. Each of the plurality of semiconductor devices 33 to 35 is electrically connected via a penetrating wiring (not illustrated).

In a manufacturing method of the image pickup apparatus 1B, a plurality of device wafers, in each of which the plurality of semiconductor devices 33 to 35 are formed, are produced. Then, the plurality of device wafers are laminated, thereby producing the laminated device wafer.

The image pickup unit 30 to which the laminated semiconductor 39 is bonded is produced by bonding and then cutting the image pickup wafer and the laminated device wafer.

There may be a case in which mechanical strength of the laminated semiconductor 39 against a stress in the direction that perpendicularly intersects the optical axis is not high. There may also be a case in which mechanical strength at a bonded portion between the image pickup unit 30 and the laminated semiconductor 39 is not high.

The image pickup apparatus 1B has high mechanical strength against a stress in the direction that perpendicularly intersects the optical axis since the image pickup unit 30 and the laminated semiconductor 39 are disposed in the second through-hole H23. In other words, the frame 23 has a reinforcing function for improving the mechanical strength of the laminated semiconductor 39. It is a matter of course that the image pickup apparatus 1B has higher performance than the image pickup apparatuses 1 and 1A since the image pickup apparatus 1B has the laminated semiconductor 39.

Note that it is not necessary for the entire laminated semiconductor 39 to be fully accommodated in the second through-hole H23, and for example, a part of the semiconductor device 35 located at the backmost surface may project from the second through-hole H23. In other words, it is only necessary for the laminated semiconductor 39 to be disposed such that at least a part of the laminated semiconductor 39 is inserted into the second through-hole H23.

The image pickup apparatus 1B is provided with a light shielding layer 70 that covers an optical side surface 10SS and a holding side surface 20SS. The light shielding layer 70 is disposed by filling a groove formed by a known step cut dicing method, for example, with a light shielding resin.

According to the step cut dicing method, the groove is formed along a cut line using a first dicing blade with a cutting margin of a first width in a process (S50) of cutting the holding wafer 29W with optical portions in which the plurality of image pickup units 30 are disposed. Then, the groove is filled with a resin containing a light shielding material such as carbon particles, for example. Then, cutting is performed using a second dicing blade with a cutting margin that is narrower than the first width, thereby producing the image pickup apparatus 1B with the light shielding layer 70 provided on the side surface. The direction in which the groove is formed using the first dicing blade may be opposite.

The light shielding layer 70 may be a metal layer disposed in the groove by a plating method or a sputtering method and may be disposed after the cutting process (S50).

The image pickup apparatus 1B provided with the light shielding layer 70 is not affected by external light and thus has high performance.

It is a matter of course that the image pickup apparatuses 1 and 1A also have the same advantages as the advantages of the image pickup apparatus 1B as long as the image pickup apparatuses 1 and 1A also include light shielding layers 70 that cover the optical side surfaces 10SS and the holding side surfaces 20SS similarly to the image pickup apparatus 1B.

Fourth Embodiment

Figure 18:
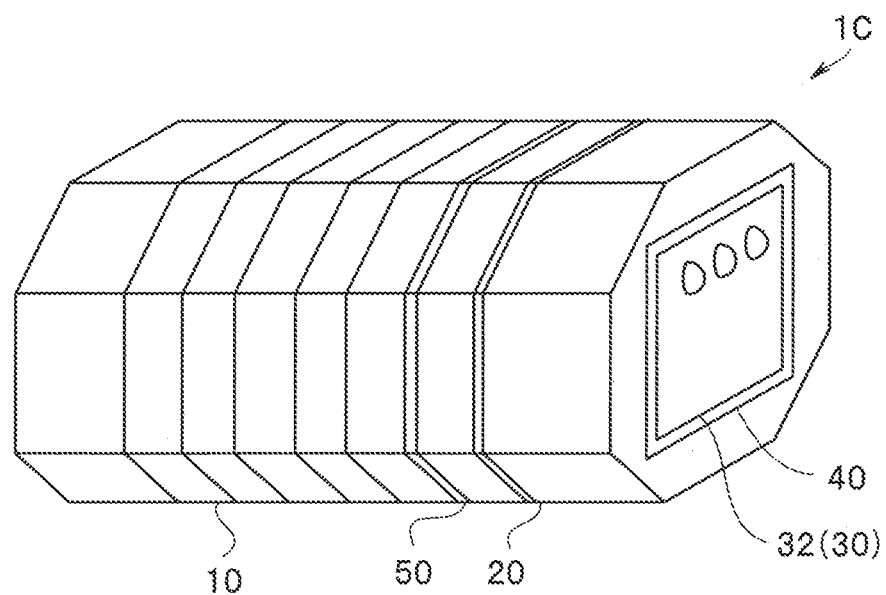
FIG. 18 is a perspective view of an image pickup apparatus according to a fourth embodiment.

In the image pickup apparatus 1C illustrated in FIG. 18, outer shapes of a laminated optical portion 10 and a holding portion 20 are hexagonal columns.

Outer shapes of the laminated optical portion and the holding portion corresponding to a wafer level laminated body are hexagonal columns obtained by chamfering corners of sides of quadrangular columns. Note that quadrangular columns may be chamfered into curved surface shapes, thereby obtaining cylindrical shapes.

Since the image pickup apparatus 1C in which the outer shapes of the laminated optical portion and the holding portion are hexagonal columns that are polygonal columns can be disposed in a space that is narrower than a space for the image pickup apparatus 1, the image pickup apparatus 1C is effective for reducing the diameter (reducing invasiveness) of the endoscope. Note that the outer shapes of the laminated optical portions 10 and the holding portions 20 in the image pickup apparatuses 1, 1A, and 1B are also not limited to the rectangular parallelepiped shapes.

Needless to say, the endoscopes that include the image pickup apparatuses 1A to 1C have the effects of the endoscope 9 that includes the image pickup apparatus 1 and further have the effects of the image pickup apparatuses 1A to 1C.

The present invention is not limited to the aforementioned embodiments, modifications, and the like, and various modifications, combinations, and applications can be made without departing from the gist of the present invention.

What is claimed is:

1. An image pickup apparatus comprising:
   a first member including an incident surface and an emission surface on an opposite side of the incident surface, the first member comprising a plurality of laminated optical members;
   a second member including a front surface and a back surface on an opposite side of the front surface, the second member comprising an image pickup device having an image sensor, a cover glass being glued to the image pickup device; and
   a third member including a spacer, the spacer including a first main surface and a second main surface on an opposite side of the first main surface, the third member having a frame including a third main surface and a fourth main surface on an opposite side of the third main surface such that the third main surface faces the second main surface,
   wherein the third member comprising:
     a first through-hole penetrating through the spacer, the first through-hole having a first sectional area in a direction that perpendicularly intersects an optical axis; and
     a second through-hole penetrating though the frame, the second through-hole having a second sectional area in the direction that perpendicularly intersects the optical axis larger than the first sectional area of the first through-hole,
   the first main surface of the third member is glued to the emission surface of the first member,
   the second member is disposed such that at least a part of the second member is inserted into the second through-hole and the front surface abuts on the second main surface of the spacer, and
   the frame is configured to shield light that is incident on the second through-hole from a side surface of the second member;
   wherein the spacer and the frame are made of silicon,
   the third member includes a silicon oxide layer that bonds the spacer and the frame, and
   the silicon oxide layer having a third through-hole having a same sectional area in the direction that perpendicularly intersects the optical axis as the second sectional area.

2. The image pickup apparatus according to claim 1, wherein a first sectional shape of the first through-hole in the direction that perpendicularly intersects the optical axis is circular, and a second sectional shape of the second through-hole in the direction that perpendicularly intersects the optical axis is rectangular.

3. The image pickup apparatus according to claim 1, further comprising an adhesive disposed between the side surface of the second member and a wall surface of the second through-hole.

4. The image pickup apparatus according to claim 1, wherein a first side surface of the first member and a second side surface of the third member are in a same plane.

5. The image pickup apparatus according to claim 4, wherein continuous cut marks are provided in the first side surface and the second side surface.

6. The image pickup apparatus according to claim 1, wherein a notch is provided at an outer peripheral edge of an opening of the second through-hole in the third main surface of the frame.

7. The image pickup apparatus according to claim 1, wherein a notch that is parallel to the optical axis is provided in a wall surface of the second through-hole in the frame.

8. The image pickup apparatus according to claim 1, further comprising a light shielding layer covering a first side surface of the first member and a second side surface of the third member.

9. The image pickup apparatus according to claim 1, further comprising:
   a laminated semiconductor, bonded to the back surface of the second member, the laminated semiconductor comprising a plurality of laminated semiconductor devices,
   at least a portion of the laminated semiconductor is inserted into the second through-hole.

10. The image pickup apparatus according to claim 1, wherein a first outer shape of the first member and a third outer shape of the third member are polygonal columns.

11. An endoscope comprising:
   an insertion section configured to be inserted into a body cavity of a subject; and
   an image pickup apparatus disposed in the insertion section, wherein the image pickup apparatus comprises:
      a first member including an incident surface and an emission surface on an opposite side of the incident surface, the first member comprising a plurality of laminated optical members,
      a second member including a front surface and a back surface on an opposite side of the front surface, the second member comprising an image pickup device having an image sensor, a cover glass, and
      a third member including a spacer, the space including a first main surface and a second main surface on an opposite side of the first main surface, the third member having a frame including a third main surface and a fourth main surface on an opposite side of the third main surface such that the third main surface faces the second main surface,
   wherein the third member comprising:
      a first through-hole penetrating through the spacer, the first through-hole having a first sectional area in a direction that perpendicularly intersects an optical axis; and
      a second through-hole penetrating though the frame, the second through-hole having a second sectional area in the direction that perpendicularly intersects the optical axis larger than the first sectional area of the first through-hole,
   the first main surface of the third member is glued to the emission surface of the first member,
   the second member is disposed such that at least a part of the second member is inserted into the second through-hole and the front surface abuts on the second main surface of the spacer, and
   the frame is configured to shield light that is incident on the second through-hole from a side surface that is a side surface of the second member;
   wherein the spacer and the frame are made of silicon,
   the third member includes a silicon oxide layer that bonds the spacer and the frame, and
   the silicon oxide layer having a third through-hole having a same sectional area in the direction that perpendicularly intersects the optical axis as the second sectional area.

12. The image pickup apparatus according to claim 1, wherein the silicon spacer is etched to form the first through-hole, the silicon frame is etched to form the second through-hole, and the silicon oxide layer is etched after the first through-hole and the second through-hole are formed to form the third through-hole.

* * * * *